United States Patent [19]
Cole et al.

[11] Patent Number: 5,611,904
[45] Date of Patent: Mar. 18, 1997

[54] ELECTROCHROMATOGRAPHY APPARATUS

[75] Inventors: Kenneth D. Cole, Gaithersburg, Md.; Heriberto Cabezas, Jr., Cincinnati, Ohio

[73] Assignee: The United States of America as represented by the Secretary of Commerce, Washington, D.C.

[21] Appl. No.: 555,449

[22] Filed: Nov. 9, 1995

[51] Int. Cl.[6] ................................................ G01N 27/26
[52] U.S. Cl. .................... 204/640; 204/450; 204/551; 204/572; 204/518; 204/627; 204/637; 204/647; 204/282; 204/260; 204/252; 204/671; 204/263; 204/264; 204/295; 204/280; 204/415; 205/775; 205/792.5; 205/793; 210/748; 210/198.2; 210/656; 210/243
[58] Field of Search ...................... 204/450, 551, 204/572, 518, 627, 632, 637, 647, 282, 260, 252, 640, 671, 263, 264, 295, 280, 415; 205/775, 792.5, 793; 210/748, 198.2, 243, 656; 422/70; 359/265

[56] References Cited

U.S. PATENT DOCUMENTS 3,725,232  4/1973  Pretorius et al. ...................... 205/775
4,285,794  8/1981  Bellows et al. ...................... 204/272

OTHER PUBLICATIONS

Basak et al., J. AIChE, 41(11), 2499–507. Nov. 1995.

*Primary Examiner*—Kathryn Gorgos
*Assistant Examiner*—Alex Noguerola
*Attorney, Agent, or Firm*—Jagtiani & Associates

[57] ABSTRACT

The invention provides fittings for the ends of electrochromatography columns. Each fitting includes an annular electrode surrounding one end of the passage electrical fields to be applied. The fitting also contains a passageway for eluant flowing into or out of the column, an annular chamber for the electrode and a membrane separating the passageway from the annular electrode chamber. The membrane prevents gases and electrolytic products from entering the column eluent going through the chromatographic column. The membrane also isolate the electrodes from the compounds such as proteins and macromolecules being separated. A buffer solution was pumped through the electrode chamber to remove the gases and electrode products. The buffer flow through the electrode chamber maintains a constant pH and conductivity so that the electrical field applied by each electrode is constant. The buffer flow also serves to remove the heat generated in the electrode chamber.

The invention also provides an electrochromatography apparatus employing these fittings.

13 Claims, 4 Drawing Sheets

ELECTROCHROMATOGRAPHY APPARATUS

CROSS-REFERENCE TO RELATED APPLICATIONS

This application makes reference to the following co-pending U.S. Applications. The first application is U.S. application Ser. No. 08/555,443, entitled "Concentration and Size Fractionation of Nucleic Acids and Viruses in Porous Media", filed Nov. 9, 1995.

BACKGROUND OF THE INVENTION

Field of the Invention

The apparatus used for early work in electrochromatography (EC) or electrophoresis in packed beds is described in Bloemendal, H., *J. Chrom.* 3 (1960) 1–10; Kunkel, H. G., and Trautman, R., *Electrophoresis, Theory, Methods, and Applications,* M. Bier, ed. (Academic Press, 1959), 225–262 and Porath, *J. Sci. Tools* 11 (2) (1964) 21–27. The early columns use either U-shaped tubes or specially constructed glass columns in which the electrodes are isolated from the column. These columns do not allow the application of the electrical field during the sample application or elution. These columns are usually operated in two steps. Samples are loaded on the column and the electrical field put on. Electrophoresis is done in the absence of any flow. After a period of electrophoresis the electrodes are removed and then flow was begun to elute the separated zones. A commercially manufactured electrophoresis column is described in Porath. This column is constructed so that the separation region containing the chromatography media is the annular space between two plastic cylinders. The top electrode is open to the separation region. The bottom electrode is isolated from the buffer coming out of the bottom of the separation system by a cylindrical membrane coaxial with the column separation region. The membrane used is a gel impregnated porous plastic. Nerenberg, S. T., and Pogojeff, B. A. (1969), *Amer. J. Clin. Path.* 51 (1960), 728–740 describe an electrochromatography column that utilizes a specialized end fitting. The end fitting uses a gel to isolate the electrodes from the chromatography column eluent. Rudge, S. R., Basak, S. K., and Ladish, M. R.. *AIChE J.,* 39 (1993), 797–808 describes using chromatography column fittings containing platinum electrodes, but the electrodes are not isolated from the chromatography column eluent. U.S. Pat. No. 3,969,218 to Scott, the entire contents and disclosure of which is hereby incorporated by reference, also describes an electrophoresis process in which the electrodes are immersed in the column eluent. When the electrodes are immersed in the column eluent, gases, electrolytic products and pH changes generated at the electrodes contaminate the buffer throughout the column. Furthermore, proteins and macromolecules which are being separated using the column may react with the electrode. For these reasons, it is undesirable to have the electrode immersed in the column eluent.

Cole, K. D. and Cabezas, H., Jr., *Appl. Biochem. Biotech.* (1995) describe an electrochromatography column that has membranes located in side-arms but the electrodes are physically distant from the chromatography media. Although physically separating the electrodes from the chromatography avoids the problems of contamination, such separation limits the effectiveness of the electrodes.

SUMMARY OF THE INVENTION

It is thus one object of the invention to provide a novel fitting for an electrochromatography column for the efficient and reliable application of electrical fields to a packed chromatography column.

The fitting includes a fluid passageway therethrough to allow eluent to flow through the fitting to the column or to allow eluent from the column through the fitting. Within the fitting, an annular electrode is suspended in an electrode chamber that annularly surrounds at least a portion of the fluid passageway. The electrode chamber includes inlet and outlet conduits which allow an electrode buffer solution to flow into and out of the electrode chamber. A membrane separates the fluid passageway from the electrode chamber. The membrane allows fluids and ions to pass between said electrode chamber and the fluid passageway, but prevents the flow of proteins, macromolecules, electrolytic products and gases between the electrode chamber and the fluid passageway.

Another object of the invention is to provide a novel electrochromatography apparatus employing two of these novel fittings, one at either end of the electrochromatography column.

Other objects and features of the present invention will be apparent from the following detailed description of the preferred embodiment.

BRIEF DESCRIPTION OF THE DRAWINGS

The invention will be further described in conjunction with the accompanying drawings, in which.

DETAILED DESCRIPTION OF THE PREFERRED EMBODIMENTS

Figure 1:
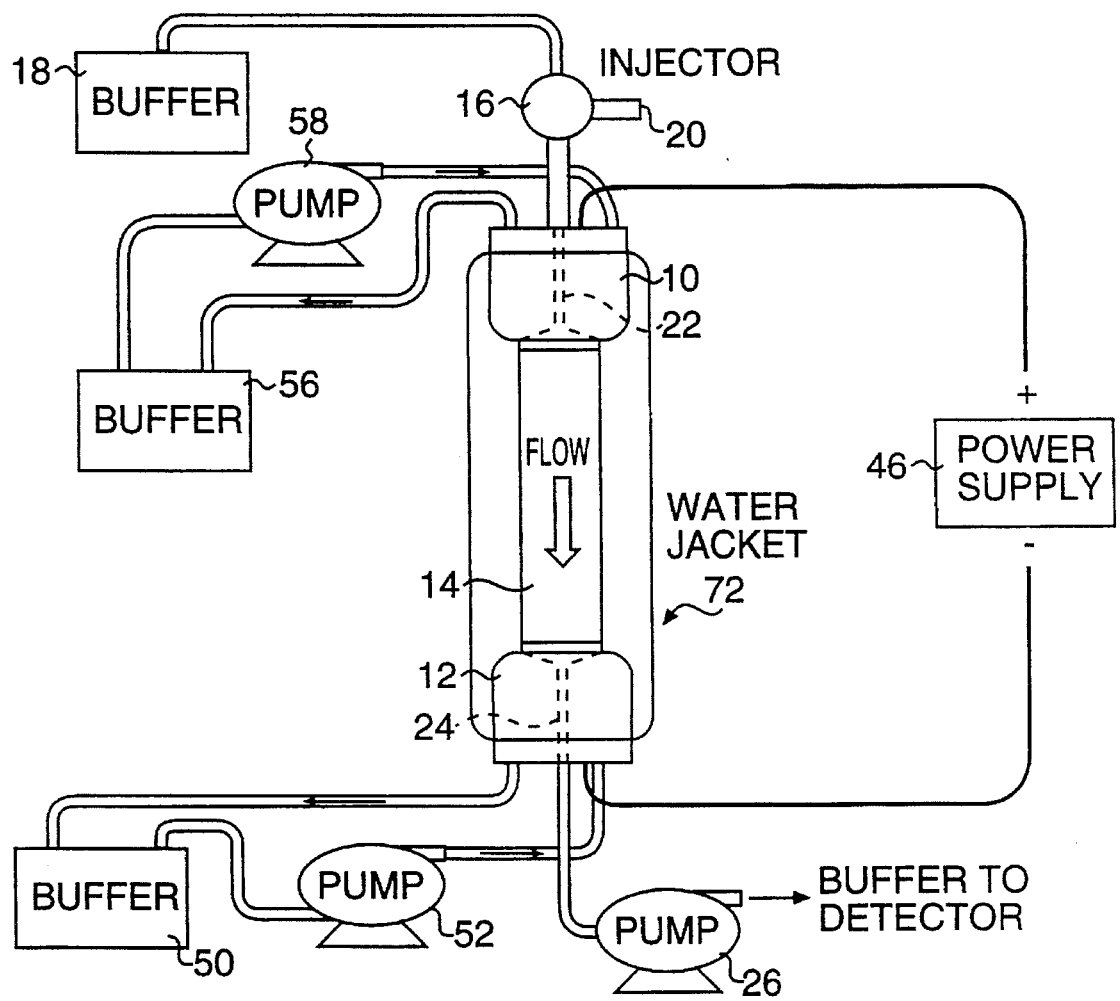
FIG. 1 is diagram of an electrochromatography apparatus in accordance with the invention.

FIG. 1 shows an electrochromatography apparatus of a preferred embodiment of the invention in which two column fittings, 10 and 12, are attached to either end of an electrochromatography column 14. Fittings 10 and 12 are preferably made of a non-conducting material such as nylon. Column 14 is filled with a known chromatography column packing medium such as porous polyethylene packing supports. An injector 16 supplies fitting 10 with eluent or column buffer solution from eluent container 18. Injector 16 also includes an inlet 20 through which a sample containing proteins, macromolecules or colloids to be separated in the column may be added to the eluent. The eluent flows through passageway 22, shown by shadow lines, and into column 14. Eluent flows through column 14 and exits the column through fitting 12 through passageway 24, shown by shadow lines, and is pumped away by pump 26. Pump 26 aids in pulling eluent through column 14.

Figure 3:
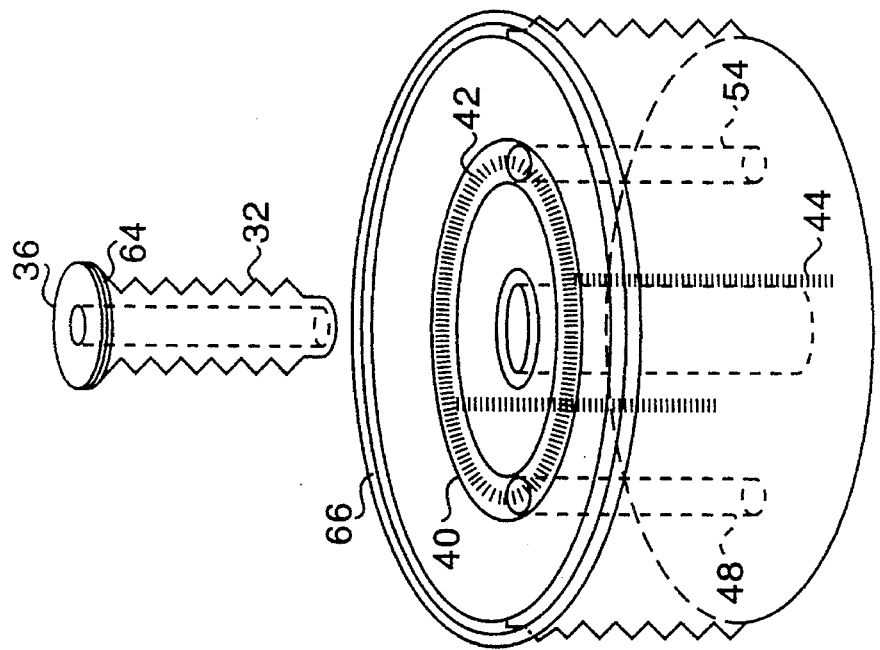
FIG. 3 is a partially exploded view of the electrochromatography column fitting of FIG. 2 with shadow lines to show interior detail. The porous bed support and membrane have been omitted for clarity.
Figure 2:
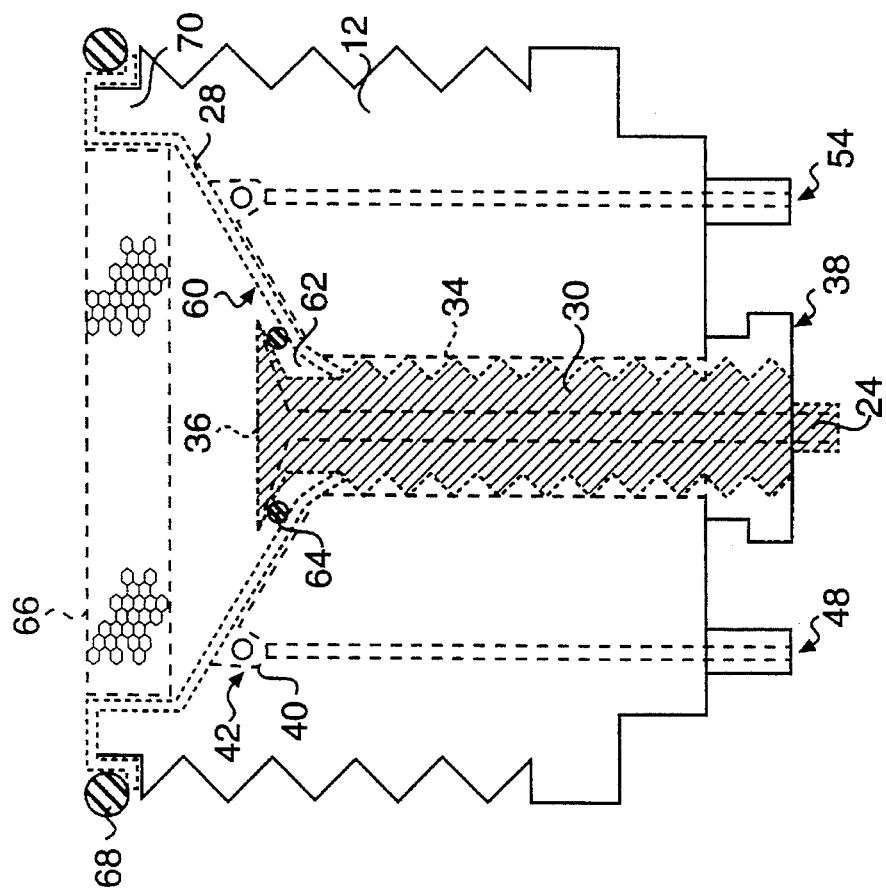
FIG. 2 is a cross section view of an electrochromatography column fitting of the invention filled with a porous bed support.

FIGS. 2 and 3 show the structure of fitting 12 in detail. Fitting 12 is identical to fitting 10, except that fitting 10 is upside down relative to fitting 12 in the apparatus shown in FIG. 1. Passageway 24 extends through fitting 12 and is divided into a frusto-conical section 28 and a cylindrical section 30. Within cylindrical section 30 there is inserted a compression insert 32 having an interior passageway 34 through which eluent passes and exits fitting 12. At the top of insert 32 is a funnel portion 36. A thumb nut 38 helps secure insert 32 in place within cylindrical section 30 of passageway 24.

In annular communication with frusto-conical section 28 of passageway 24 is an annular electrode chamber 40 in which a annular electrode 42 is suspended. Electrode 42 is connected by electrical connection 44 to power supply 46. Power supply 46 is also connected to an electrode (not shown) in fitting 10. When power supply 46 is turned on, a potential difference is set up between the electrodes and is applied across the length of column 14. This potential difference causes one end of the column to be electrolytically positive relative to the other end. When a sample containing macromolecules flows through eluent in column 14, charged macromolecules flow towards the end of column 14 having the opposite charge to their own charge. The actual separation of the macromolecules in the sample depends upon the different macromolecules in the sample moving at different rates because of differing charges and sizes.

Electrode chamber 40 is supplied through buffer inlet 48 with a buffer solution from buffer container 50 by pump 52. Buffer solution returns to buffer container 50 by way of buffer outlet 54. An electrode chamber (not shown) in fitting 10 is similarly supplied with a buffer solution from buffer container 56 by pump 58. The buffer solution for electrode chamber 40 may have the same or a different composition from that of the eluent for column 14. By circulating buffer solution through electrode chamber 40, electrolytic products produced at electrode 42 are removed from electrode 42. As shown in FIG. 1, buffer solution used in electrode chamber 40 is circulated and recycled in order to conserve buffer solution. However, it is also contemplated that in some embodiments of the invention it may be desirable to continuously supply new buffer solution to electrode chamber 40 in order to avoid contamination of electrode 42 by previously used buffer solution.

Membrane 60 may be formed from a conventional dialysis membrane having a hole 62 in its center through which compression insert 32 is inserted as shown in FIG. 2. Compression insert 32 is provided with an inner O-ring 64 around the base of funnel portion 36 which presses against membrane 60. Thumb nut 38 is tightened to compress inner O-ring 64 against membrane 60 and secure membrane 60 to frusto-conical section 28. When membrane 60 is in place as shown in FIG. 2, it separates passageway 24 containing column eluent from electrode chamber 40 containing electrode buffer solution. Membrane 60 allows ions to pass between electrode chamber 40 and passageway 24 so that an electric field may be uniformly applied to column eluent. However, membrane 60 prevents electrolytic products and gases formed at electrode 42 from reaching column eluent in passageway 24. Membrane 60 also prevents macromolecules in the eluent from reaching electrode 42. Although the use of a dialysis membrane to isolate the electrode has been described, any suitable membrane type such as ultrafiltration, reverse-osmosis, or ion-exchange may be used for membrane 60.

Porous bed support 66 is deposited on top of membrane 60 further sealing it to the walls of frusto-conical section 28. Porous bed support 66 may have the same composition as or be different from the porous packing medium used in column 14.

Outer O-ring 68 is slipped over the membrane 60 and column fitting lip 70 of fitting 12. Fitting 12 is joined to column 14 by screwing fitting 12 into column 14 until O-ring 68 is compressed against the bottom end of column 14. This compresses the O-ring against membrane 60 and column fitting lip 70, sealing membrane 60 on its outer edge. A water jacket surrounds column 14 to maintain the interior portion of column 14 at a fixed temperature. It should be appreciated that if the electrical fields that are used, are low, then it is not necessary to use the water jacket to remove heat.

The electrochromatography apparatus of the invention allows a lot of flexibility. The column end fittings are easily exchanged to new columns of different length. Also different column diameters may be used with fittings; made using the same design. The use of separate buffer containers for the electrode and the column allow the use of buffers for the electrode that do not have high buffering capacity. Large external buffer containers may be used for the electrode chamber buffer container to allow the buffers to be checked for any changes in pH or conductivity and kept at a constant temperature. The circulation rate of the electrode chambers may also be set independently of the flow rate in the column.

The electrochromatography apparatus of the invention has significant advantages over conventional EC columns. The isolated electrode chamber is in close proximity to the packed bed of the column and provides a uniform field to the column. The use of this electrode chamber also allows most of the power to be across the chromatography media. The isolated chambers use membranes to allow the passage of the electrical field but prevent macromolecules from coming into contact with the electrode surfaces. Continuous operation of the electrical field during sample loading and elution is possible because of the isolation feature. The small volume of the electrode chamber combined with a large external electrode buffer volume allow the use of low conductivity buffers, which may not have a large buffering capacity. The rapid flow through the small volume electrode chamber removes electrode gases which if present would prevent the passage of current. The buffer flow also helps to maintain a constant pH and conductivity in the electrode chamber, results in a constant electrical field. The buffer flow also serves to remove heat generated in the electrode chamber.

The construction of the EC fitting described in this report may be applied to other fittings with minor modifications. The fittings do not adversely effect the chromatic performance of the column and allow the adaptation of existing equipment for EC. The ease of use and reliable performance of these columns should encourage the use of EC for the separation of a wide variety of compounds.

Having generally described the apparatus of the invention, the following examples are given as further illustration thereof.

EXAMPLE 1

Materials

Nylon Chromatography Fittings (No. 5837) for 15 and 25 mm threads, porous polyethylene packing supports (100 μm pores), O-rings, and water-jacketed glass columns were obtained from Ace Glass Inc. (Vineland, N.J.). Water-jacketed columns were also made by a glass blower using Ace Glass fittings. Nylon machine screws, thumb nuts, miniature tubing fittings, and O-rings were from Small Parts Inc., (Miami, Fla.). Dialysis membrane (Spectrapore 1, 6,000–8,000 molecular weight cutoff) was from Spectrum Medical Industries (Los Angeles). Sephadex G-25 fine (20–80 μm dry bead diameter), Sephadex G-75 (40–120 μm dry bead diameter), myoglobin (horse heart), and β-lactoglobulin (bovine) were obtained from Sigma Chemical Co. (St. Louis, Mo.).

Construction of the Fittings

The electrochromatography column fittings are designed to apply an electrical field across a packed bed in a chromatography column as shown in FIG. 1. The commercial nylon fittings were modified to provide an isolated electrophoresis chamber just below the bed support position (FIGS. 2 and 3). Two sizes of fittings were modified and the dimensions are given for the 25 mm fitting followed by dimensions for the 15 mm fitting. A circular groove was machined concentric to the outlet/inlet center hole with a radius of 19 mm (11 mm for the 15 mm fittings) on the surface below the bed support position. The groove had a depth of 2.5 mm and a width of 2.5 mm (depth of 1.5 mm and width of 1.5 mm width for the 15 mm fittings). In the bottom of the groove four 2.4 mm (3/32 in.) holes were drilled through the fittings parallel to the center line and spaced 90° apart. Holes for the 15 mm fitting were 1.6 mm (1/16 in.) The outlet/inlet hole was drilled to 6.4 mm (1/4 in.) and counter sunk at 82°. On the smaller 15 mm fittings the countersink is stopped short of breaking into the machined groove.

Two lengths (approximately 150 mm) of platinum wire with a diameter of 0.4 mm were twisted together on the ends to form a central loop region. The twisted ends of which were inserted in two opposite holes in the groove and the central loop was pushed into the bottom of the groove. The twisted ends of the wires were sealed into the holes using silicone rubber adhesive (RTV 108, GE Silicones, Waterford, N.Y.). This was accomplished by using a large bore needle and syringe filled with the adhesive. Care was taken not to block the groove or coat the platinum wires exposed in the grove that forms the electrode chamber. One end of the protruding platinum wire was soldered to a female banana plug and heat shrink tubing added to insulate the wire. The other end of the wire was sealed with heat shrink tubing. The other two open holes in the groove comprise the electrode chamber inlet and outlet. The external side of the inlet and outlet hole is drilled and tapped to accept a 2.4 mm (3/32 in.) threaded hose barb. Because of the smaller diameter of the 15 mm fitting, 90° elbow fittings with inside diameter of 1.6 mm (1/16 in.) were fitted to exit on the side of the tubing below the surface where the thumb nut will tighten. The fittings were sealed in place with silicone rubber adhesive.

The central compression insert was made from a 6.4 mm×50.8 mm (1/4×2 in.) nylon machine screw. A 2.4 mm diameter hole (1.6 mm for the 15 mm fittings) was drilled through the central axis of the screw. A portion (approximately 6 mm) of the threaded end of the screw was ground down to provide a nipple that tubing may be slipped on. The final diameter of the nipple end was approximately 4 mm. The diameter of the head of the screws used in the 15 mm fittings were reduced to 9.5 mm. The upper surface of the head of the screw was tapered to provide a draining surface that approximates the original contour of the fitting. This was accomplished using a small rotary grinder to remove the nylon in the center of the screw head. The countersink surface of the screw was polished to remove any ridges. A small O-ring, 6 mm. inside diameter, width 1.8 mm (4.5 mm inside diameter, 1.8 mm width for the 15 mm fittings), was slipped on to just below the head of the central compression insert.

Assembly of the Column Fittings

A hole was punched in wetted dialysis membrane using a 6.4 mm diameter cork bore. The central compression insert was inserted into the hole of a single layer of dialysis membrane until the membrane is against the O-ring. The central compression insert and membrane was inserted into the column fitting. A thumb screw was tightened to compress the central O-ring against the membrane and the body of the column fitting. Care was taken to keep the membrane wet and free of wrinkles when it is compressed. A wetted bed support was pressed into position sealing the membrane on the perimeter of the column fitting lip. The thickness of the porous bed support used in the 15 mm columns was reduced to a thickness of approximately 1.3 mm by cutting the supplied supports in half with a razor blade. The outer O-ring, 26.6 mm inside diameter, 2.6 mm width (14 mm inside diameter, 1.8 mm width for the 15 mm fitting) was slipped over the wet membrane and on to the outer lip of the fitting. The dialysis membrane was trimmed so that only a small portion protruded beyond the outer O-ring. The assembled fitting was then carefully screwed into the column until the O-ring was compressed against the glass shoulder of the column sealing the membrane against the fitting. The electrode buffer recirculation pump was started and operated for approximately 10 minutes to observe for leaks. If the membrane was not properly sealed, buffer begins to drip out of the inlet/outlet.

Operation of the Column

The water-jacketed column was maintained at 25° C. with an inside diameter of 1.5 cm and a length of either 10.2 cm or 30 cm (between bed supports). A peristaltic pump placed at the outlet of the column was used to maintain a constant flow rate. The eluent was monitored at 230 nm by a UV detector. The electrode buffers were circulated to 1 liter buffer containers (25° C.) by means of a peristaltic pump. Each fitting was maintained as an independent loop (1 l of buffer) and circulated with a flow rate of 15 ml/min.

EXAMPLE 2

An important consideration of the column fitting is that they do not adversely effect the chromatographic performance of the column. Table 1 shows the theoretical plates obtained using β-lactoglobulin (excluded from the gel) and glycine (totally included in the gel) on columns packed with Sephadex G-25 fine and using an a fitting of the invention and conventional column fitting.

TABLE 1

Number of theoretical plates (N) obtained from 1.5 × 10.2 cm column packed with Sephadex G-25, Fine using a fitting of the invention and a conventional fitting.

| Fitting | β-Lactoglobulin N ± S.D. | Glycine N ± S.D. |
| --- | --- | --- |
| Invention | 241.0 ± 8.6 | 457.0 ± 9.6 |
| Conventional | 241.3 ± 22.1 | 477.3 ± 30.9 |

Figure 4:
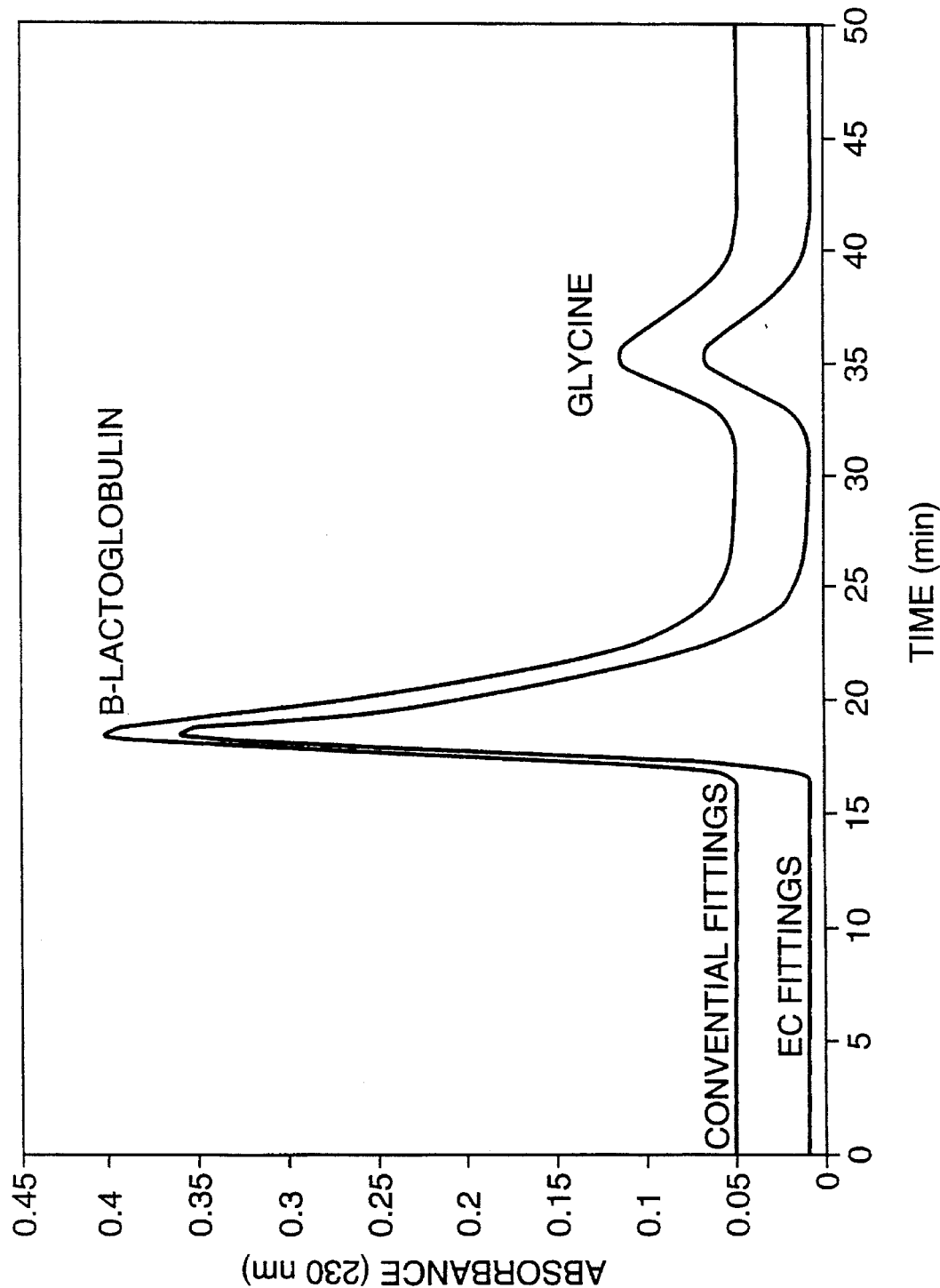
FIG. 4 is graph of the peak shapes of $\beta$-lactoglobulin and glycine obtained with an electrochromatography column of the invention and with a conventional column.

Values are means of 3 determinations, ±S. D. (the standard deviation). FIG. 4 shows the peaks shapes of β-lactoglobulin and Glycine obtained with both types of fittings. The two types of fitting gave same the same results. Both columns were maintained at 25° C. with a flow rate of 0.5 ml/min. The sample was 0.25 ml of β-lactoglobulin (1 mg/ml) and glycine (470 mM). The buffer was 3.9 mM tris(hydroxy)amino methane, 47 mM glycine, 0.25 mM ethylene-diaminetetraacetic acid, pH 8.2.

EXAMPLE 3

Figure 5:
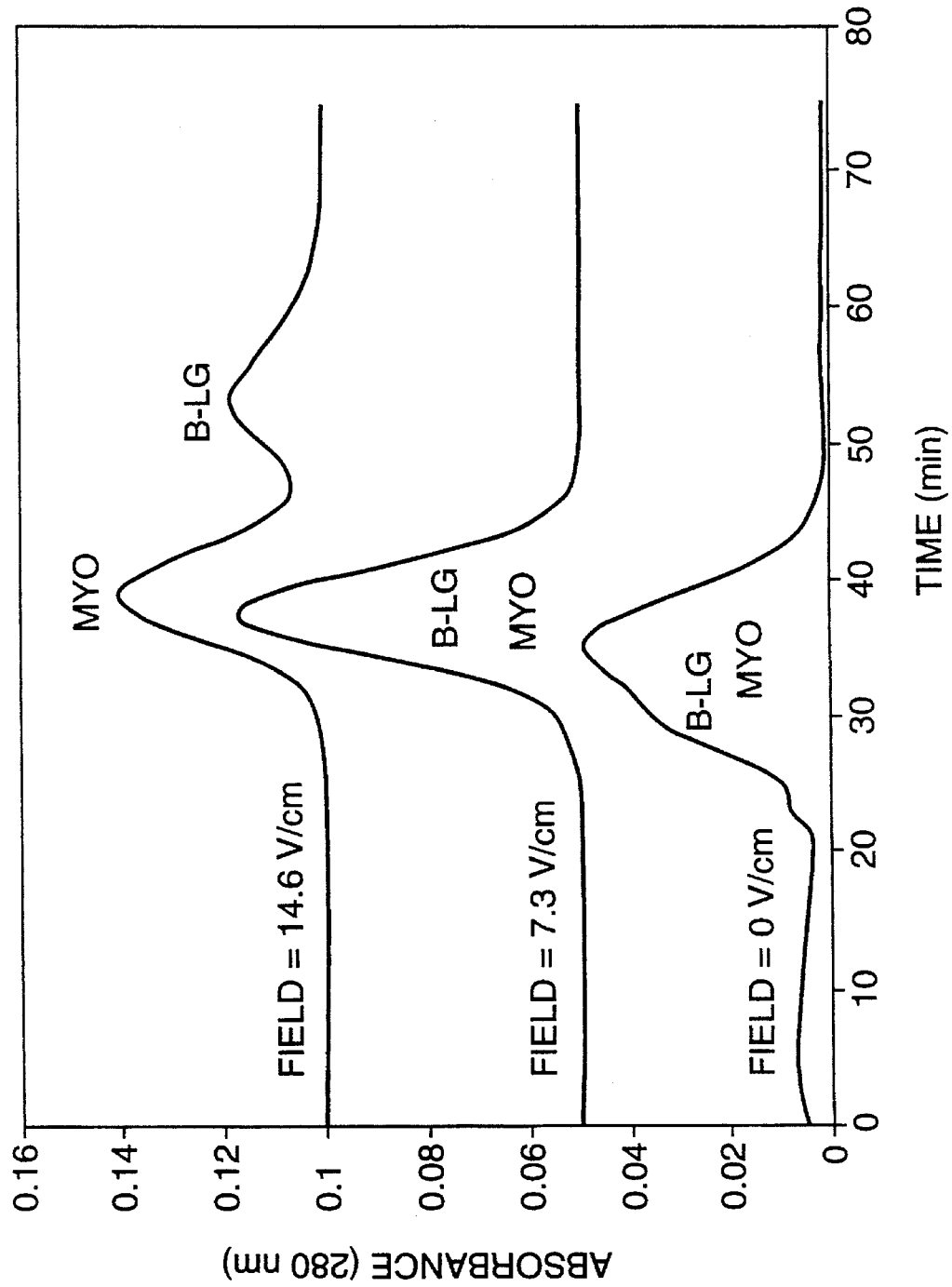
FIG. 5 is a graph showing the electrochromatography separation of proteins using an electrochromatography column of the invention.

FIG. 5 is a graph of an electrochromatography separation of proteins using an apparatus of the invention. Bovine β-lactoglobulin (B-LG) and horse heart myoglobin (MYO) 0.5 mg of each injected on the column (1.5×30 cm) packed with Sephadex G-75. The flow rate was 1.0 ml/min maintained at 25° C. electrical field strengths (E) were calculated by the formula, $E=I/A \cdot k$, where I is the current and A is the cross section area of the column and k is the conductivity of the buffer (174 μS at 25° C.). The buffer was the same as described in Example 2.

β-lactoglobulin and myoglobin do not normally separate under these conditions (a 1.5×30 cm column packed with Sephadex G-75). β-lactoglobulin has an electrophoretic mobility approximately 4.5-fold higher than myoglobin as described in Cole, K. D., Todd, P., Srinivasan, K. and Dutta, B. K. (1995) *J. Chrom. A* (1995) 707, 77–85. When moderately high electrical fields are applied (negative electrode at the column inlet) β-lactoglobulin is retained on the column much longer than myoglobin, the protein with lower electrophoretic mobility, and thus the two proteins may be separated.

What is claimed is:

1. A fitting for an electrochromatography apparatus comprising:

a fitting body comprised of a non-conducting material for attaching to one end of an electrochromatography column, said fitting body including:

a fluid passageway extending through said fitting body for communicating with the electrochromatography column; and an electrode chamber within said fitting body annularly surrounding at least a portion of said fluid passageway, said electrode chamber including inlet and outlet conduits which allow an electrode buffer solution to flow into and out of said electrode chamber;

an electrode for applying an electric field to said fluid passageway, said electrode being suspended in said electrode chamber and annularly surrounding at least a portion of said fluid passageway; and a membrane separating said fluid passageway from said electrode chamber, said membrane allowing fluids and ions to pass between said electrode chamber and said fluid passageway and preventing the flow of electrolytic products, gases, proteins and macromolecules between said electrode chamber and said fluid passageway.

2. The fitting of claim 1 further comprising an eluent present in said fluid passageway and an electrode buffer solution present in said electrode chamber.

3. The fitting of claim 2, wherein said eluent and said electrode buffer solution have the same composition.

4. The fitting of claim 2, further comprising a buffer container for supplying electrode buffer solution to said electrode chamber and means for circulating electrode buffer solution between said electrode chamber and said buffer container to remove heat and gases from said electrode chamber.

5. The fitting of claim 2, further comprising a buffer container for supplying only fresh electrode buffer solution to said electrode chamber and means for removing used electrode buffer solution from said electrode chamber to remove heat and gases from said electrode chamber.

6. The electrochromatography apparatus of claim 2, wherein said column eluent and said electrode buffer solution have the same composition.

7. The fitting of claim 1, wherein said fluid passageway comprises:

an outer passageway including a frusto-conical portion connected to a cylindrical portion, said frusto-conical portion including an annular passageway communicating with said electrode chamber, and a compression insert inserted into the cylindrical portion of said fluid passageway, said compression insert including a column eluent passageway therethrough and funnel portion connected to said column eluent passageway; and a porous bed support on top of said membrane filling said frusto-conical section, wherein said membrane is held in place on said frusto-conical portion by said compression insert and said porous bed support.

8. The electrochromatography apparatus of claim 1, further comprising a column eluent present in said fluid passageway and an electrode buffer solution present in said electrode chambers.

9. An electrochromatography apparatus comprising:

an electrochromatography column containing a particulate medium;

two fittings connected to respective ends of said electrochromatography column, each of said fittings comprising:

a fitting body comprised of a non-conducting material which is attached one of said respective ends of said electrochromatography column, said fitting body including:

a fluid passageway extending through said fitting body which communicates with said electrochromatography column; and an electrode chamber within said fitting body annularly surrounding at least a portion of said fluid passageway, said electrode chamber including inlet and outlet conduits which allow an electrode buffer solution to flow into and out of said electrode chamber;

an electrode for applying an electric field to said fluid passageway, said electrode being suspended in said electrode chamber and annularly surrounding at least a portion of said fluid passageway;

electrode buffer inlet means for supplying said electrode chamber with the electrode buffer solution and electrode buffer outlet means for extracting electrode buffer solution from said electrode chamber;

a membrane separating said fluid passageway from said electrode chamber, said membrane allowing fluids and ions to pass between said electrode chamber and said fluid passageway and preventing the flow of electrolytic products, gases, proteins and macromolecules between said electrode chamber and said fluid passageway;

said electrodes of said fittings applying an electric potential difference across the length of said column;

column eluent inlet means for supplying said column with a column eluent through one of said fittings;

column eluent outlet means for extracting column eluent from said column through the other of said fittings; and means for injecting a sample to be separated into said apparatus.

10. The electrochromatography apparatus of claim 7, wherein
said fluid passageway of each said fitting comprises:
- an outer passageway including a frusto-conical portion connected to a cylindrical portion, said frusto-conical portion including an annular passageway communicating with said electrode chamber, and
- a compression insert inserted into the cylindrical portion of said fluid passageway, said compression insert including a column eluent passageway therethrough and funnel portion connected to said column eluent passageway; and
- a porous bed support on top of said membrane filling said frusto-conical section, wherein said membrane is held in place on said frusto-conical portion by said compression insert and said porous bed support.

11. The electrochromatography apparatus of claim 7 wherein said column is surrounded throughout its length by cooling means for maintaining the temperature inside the column.

12. The electrochromatography apparatus of claim 7, wherein each of said electrode buffer inlet means comprises an electrode buffer container and each of said electrode buffer inlet means is connected to a respective one of said electrode buffer outlet means to circulate electrode buffer solution between said electrode chamber and said buffer container to remove heat and gases from said electrode chamber.

13. The electrochromatography apparatus of claim 7, wherein each of said electrode buffer inlet means supplies only fresh buffer solution to said electrode chamber.

* * * * *